(12) United States Patent
Krause

(10) Patent No.: US 11,071,447 B2
(45) Date of Patent: Jul. 27, 2021

(54) LARYNGOSCOPE BLADE AND METHOD FOR PRODUCING A LARYNGOSCOPE BLADE

(71) Applicant: Karl Storz SE & Co. KG, Tuttlingen (DE)

(72) Inventor: Bernd Krause, Tuttlingen (DE)

(73) Assignee: Karl Storz SE & Co. KG, Tuttlingen (DE)

( * ) Notice: Subject to any disclaimer, the term of this patent is extended or adjusted under 35 U.S.C. 154(b) by 0 days.

(21) Appl. No.: 16/191,904

(22) Filed: Nov. 15, 2018

(65) Prior Publication Data

US 2019/0159667 A1 May 30, 2019

(30) Foreign Application Priority Data

Nov. 28, 2017 (DE) .......................... 10 2017 010 987
Oct. 22, 2018 (EP) ...................................... 18000819

(51) Int. Cl.

| A61B 1/00 | (2006.01) |
|---|---|
| A61B 17/00 | (2006.01) |
| A61B 1/267 | (2006.01) |
| A61B 1/07 | (2006.01) |
| A61B 17/24 | (2006.01) |

(52) U.S. Cl.
CPC ............ *A61B 1/267* (2013.01); *A61B 1/0011* (2013.01); *A61B 1/00073* (2013.01); *A61B 1/07* (2013.01); *A61B 17/24* (2013.01); *A61B 2017/242* (2013.01)

(58) Field of Classification Search
CPC ...... A61B 1/276; A61B 1/2673; A61B 1/2676
See application file for complete search history.

(56) References Cited

U.S. PATENT DOCUMENTS

| 2,911,968 A * | 11/1959 | Schueler ............ A61B 1/00039 600/187 |
|---|---|---|
| 3,986,854 A | 10/1976 | Scrivo et al. |
| 4,516,716 A * | 5/1985 | Coad ........................ B23K 1/00 219/85.2 |
| 4,556,052 A * | 12/1985 | Muller ................... A61B 1/267 600/193 |
| 4,958,624 A | 9/1990 | Stone et al. |
| 5,993,383 A * | 11/1999 | Haase .................. A61B 1/2673 600/190 |

(Continued)

FOREIGN PATENT DOCUMENTS

| CN | 1209044 A | 2/1999 |
|---|---|---|
| CN | 104254422 A | 12/2014 |

(Continued)

*Primary Examiner* — Matthew J Lawson
*Assistant Examiner* — Lisa Nguyen
(74) *Attorney, Agent, or Firm* — Whitmyer IP Group LLC

(57) ABSTRACT

A method for producing a laryngoscope blade and a laryngoscope blade including a base blade and a tube which is arranged at least in part on an outer face of the base blade, extends approximately in a longitudinal direction of the base blade and is firmly connected to the base blade, wherein the tube, at its side facing toward the base blade, has at least in part a longitudinally extending corrugation which, with the outer face of the base blade, forms a longitudinally extending cavity, wherein the tube is connected to the base blade by a respective soldering seam in the lateral edge regions of the corrugation.

17 Claims, 4 Drawing Sheets

(56) References Cited

U.S. PATENT DOCUMENTS

| | | | |
|---|---|---|---|
| 6,174,281 B1 * | 1/2001 | Abramowitz | A61B 1/2673 600/196 |
| 6,246,061 B1 | 6/2001 | Ramsey et al. | |
| 6,248,061 B1 * | 6/2001 | Cook, Jr. | A61B 1/267 600/187 |
| 6,379,296 B1 * | 4/2002 | Baggett | A61B 1/303 600/178 |
| 2017/0035269 A1 | 2/2017 | Krause | |

FOREIGN PATENT DOCUMENTS

| | | |
|---|---|---|
| DE | 102012204178 B3 | 3/2013 |
| EP | 3127645 A1 | 2/2017 |

* cited by examiner

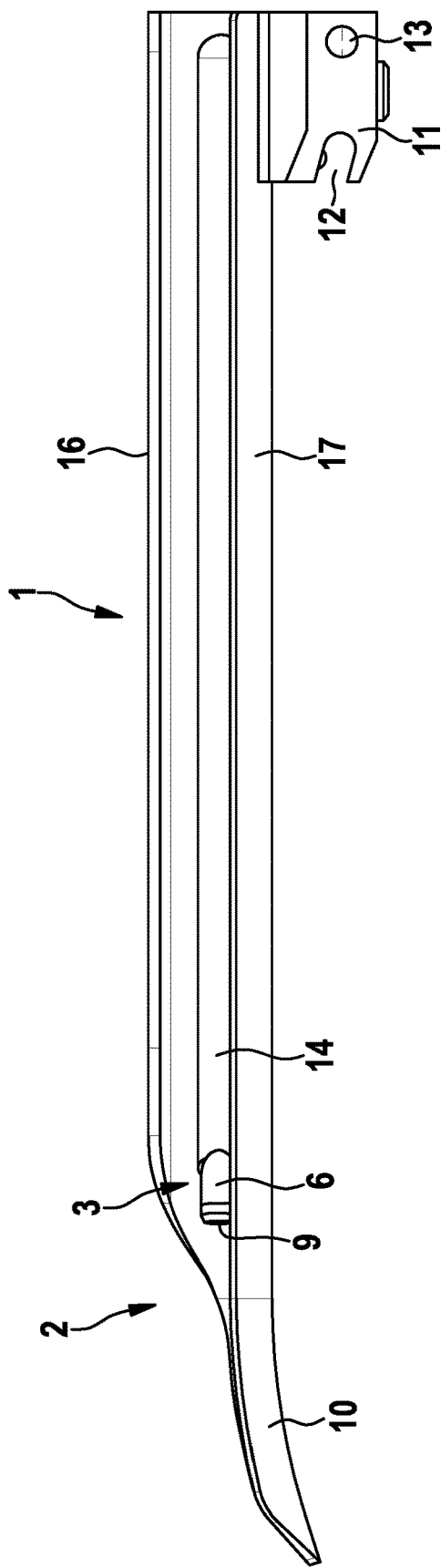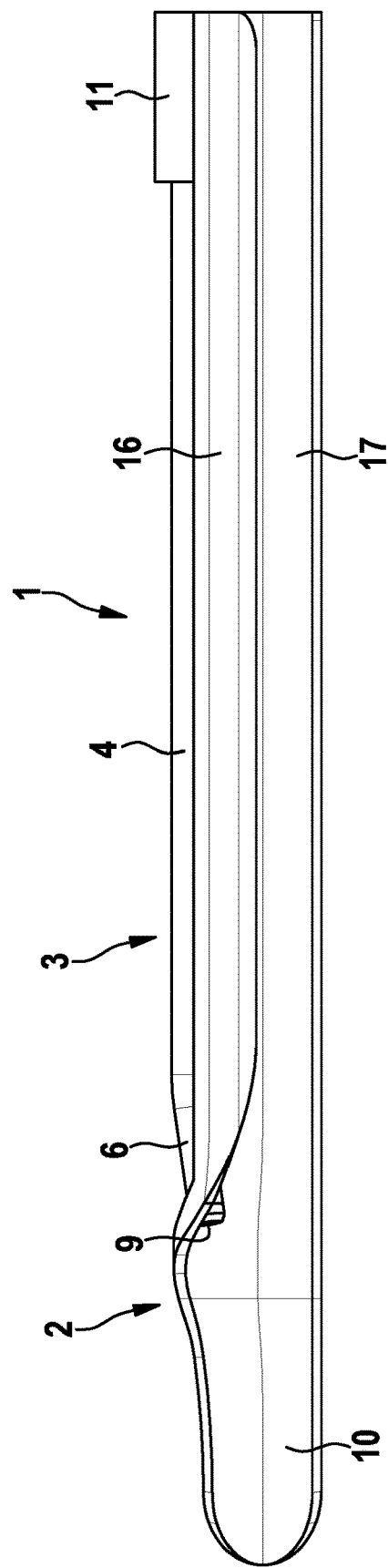

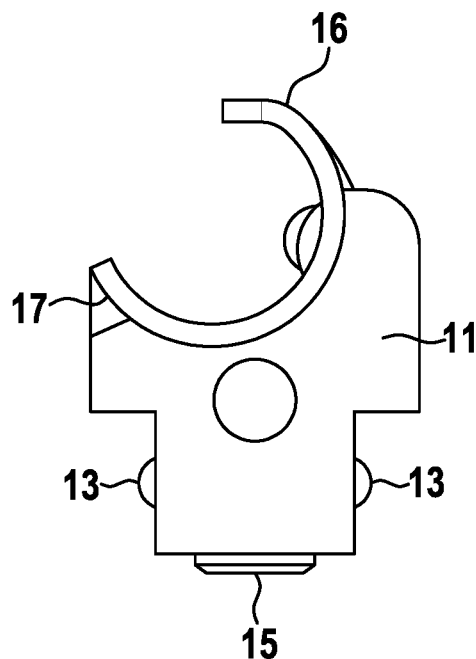
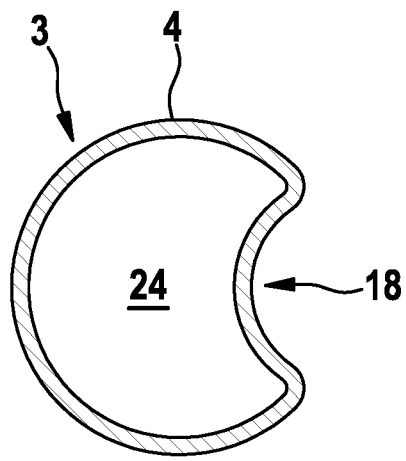
Fig. 2c   Fig. 3
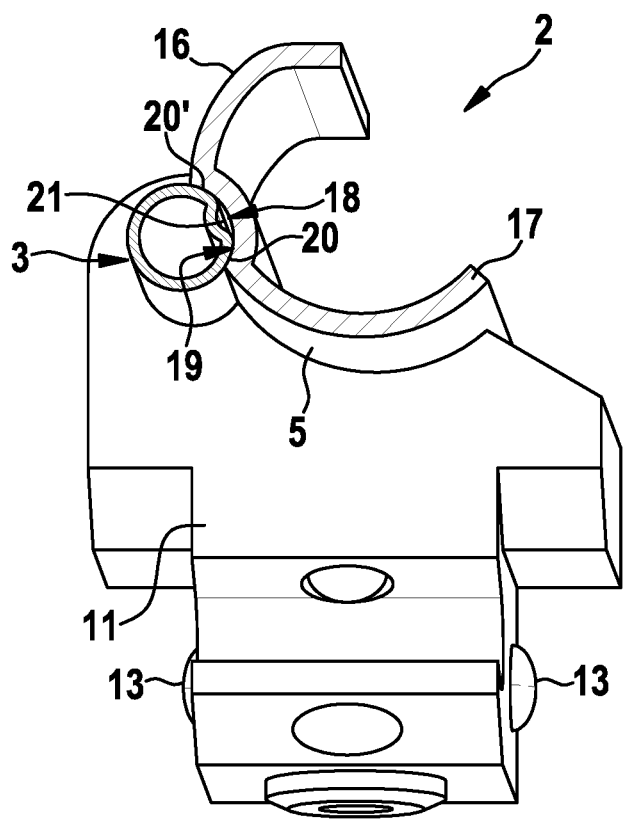
Fig. 4

LARYNGOSCOPE BLADE AND METHOD FOR PRODUCING A LARYNGOSCOPE BLADE

TECHNICAL FIELD

The present invention relates to a laryngoscope blade, in particular to a Miller laryngoscope blade, and to a method for producing such a laryngoscope blade.

BACKGROUND

Medical instruments, in particular invasive medical instruments, which are intended to be introduced into a human or animal body, are subject to special requirements. For reasons of mechanical and thermal loading, such instruments are often produced using metallic materials. In particular, the materials forming the outer surfaces of the instrument have to be biocompatible. If, for structural reasons, the medical instrument is made up of a plurality of individual components, a permanent connection of the components to one another is necessary. The connection has to have the required strength and also provide sufficient resistance to chemical and thermal influences. The outer surfaces of the instrument that result from the connection, for example soldering seams or welding seams, also have to meet the requirements of biocompatibility. These requirements apply even more in the case of reusable medical instruments, which have to be suitable for cleaning and sterilizing, in the process of which they are exposed to chemically aggressive substances and, during autoclaving, to an elevated temperature and elevated pressure.

U.S. Pat. No. 6,248,061 B1 discloses a Miller laryngoscope blade which has a substantially straight blade portion, and a base portion which is arranged near the proximal end of the blade portion and to which a handle can be attached. At a side opposite the base portion, a suction tube is secured firmly to an outer surface of the blade portion by welding. However, weld seams are not generally completely free of gaps, such that adequate cleaning and sterilizing, as is needed for repeat use, is made difficult.

According to EP 3 127 645 A1, which document is herewith incorporated by reference into the present application, a laryngoscope blade has a base blade and a cover blade which form a longitudinally extending cavity delimited in a fluid-tight manner by at least one soldering seam formed by a solder material, wherein the solder material is an iron-based solder. The cavity serves to receive optical and/or electronic components. In order to produce the laryngoscope blade, the base blade and the cover blade are connected to each other by laser spot welding, and iron-based solder is introduced in the form of a paste into the cavity formed by the base blade and the cover blade. The solder bond is introduced into a furnace and heated to a soldering temperature. In further production steps, optical and electronic components can be introduced into the cavity. The type of laryngoscope blade described in EP 3 127 645 A1 and the described production method are not optimal for a Miller laryngoscope blade.

In the patent specification DE 10 2012 204 178 B3, the subject matter of which is not of the type in question here, a microstructure component is disclosed which has microstructured plates and unstructured plates stacked alternately one on top of the other, wherein the microstructured plates have a wave profile that respectively has furrow-shaped depressions in the region of the crests, wherein between the microstructured plates and the unstructured plates there are soldered connections, which fill the furrow-shaped depressions.

SUMMARY

It is an object of the present invention to make available an improved laryngoscope blade, in particular a Miller laryngoscope blade, which can be produced in a simple and reliable way, and also a simple and reliable method for producing such a laryngoscope blade.

This object is achieved by a device, and by a method according to the invention.

Advantageous developments of the invention are set forth in the dependent claims.

A laryngoscope blade according to the invention comprises a base blade and a tube which is firmly connected to the base blade, is arranged at least in part on an outer face of the base blade and extends substantially in a longitudinal direction of the base blade. The laryngoscope blade is preferably a Miller laryngoscope blade in which the base blade is substantially straight, and wherein the base blade forms the actual blade part of the laryngoscope blade. The base blade has an outer face and an inside, wherein the outer face can serve to rest on or retain tissue, and the inside can serve to ensure a user's view into the airways of the patient. For this purpose, the base blade can be of a curved configuration in cross section and can have a continuous interior extending in the longitudinal direction. At a proximal end of the base blade, i.e. at an end near the user, a blade head can be arranged which serves for connection to a handle. The distal end of the base blade, i.e. the end remote from the user, is preferably rounded to prevent trauma.

The tube firmly connected to the base blade is in particular a light channel tube for receiving optical waveguides via which the illumination light generated by a light source is conveyed from the proximal end region of the laryngoscope blade to the distal end region. However, the tube can also be configured, for example, for receiving electrical lines or as a suction tube. The tube can have a substantially cylindrical shape; in particular, the tube is closed all the way round the circumference and, for example, only has openings at its distal end and at its proximal end. The tube preferably extends proximally onto or into the blade head. The tube has in particular a smaller cross-sectional dimension than the base blade; for example, a diameter of the tube can be considerably smaller than a width of the base blade.

According to the invention, the tube, at its side facing toward the base blade, has a longitudinally extending corrugation which, with the outer face of the base blade, forms a longitudinally extending cavity. The corrugation can extend in the form of a furrow-like depression in the wall of the tube along the entire length of the tube or only over a portion of the tube. In particular, the tube has a concave circumferential portion in a cross section in the region of the corrugation and otherwise has a convex circumferential line, wherein a radius of curvature of the circumferential line inside the corrugation is smaller than an outer radius of the base blade in the region of the outer face directed toward the corrugation, if this region is convex in cross section.

Furthermore, according to the invention, the tube is connected to the base blade by a soldering seam in the two lateral edge regions of the corrugation. Thus, in the two edge regions of the corrugation of the tube, the tube forms a longitudinally extending soldering gap with the outer face of the base blade, which soldering gap is in each case filled by a soldering seam, as a result of which the tube is firmly connected to the base blade. In particular, the longitudinal edges of the corrugation of the tube form joining regions, which interact with corresponding joining regions of the outer face of the base blade in order in each case to form a soldering gap which is filled at least partially by a solder material. The cavity formed between the tube and the base blade is in this case arranged between the joining regions or the soldering gaps. The base blade and the tube can have further portions in which the tube is not arranged on the outer face of the base blade and/or the tube is not connected to the base blade via the longitudinally extending soldering seams. Preferably, both the base blade and the tube are made of stainless steel at least in the joining regions.

By virtue of the fact that the tube bears with a longitudinally extending corrugation on the outer face of the base blade, a longitudinally extending cavity is formed which, in the production of the laryngoscope blade, serves to receive solder material which, in the soldering process, fills the soldering gaps formed in the edge region of the corrugation. This makes it possible to arrange at least some of the solder material inside the cavity adjacent to the soldering gaps, as a result of which the reliability of the soldering process can be improved in a simple manner.

In particular, by virtue of the fact that the solder material can be arranged at least in part inside the cavity, it is possible that the solder material is drawn by capillary forces into the soldering gaps and largely fills these, such that a soldering seam free of gaps is obtained. In this way, a firm connection of the tube to the base blade can be achieved in a simple and reliable manner, and, in addition, the leaktightness of the tube is maintained, the interior of which tube is available to receive optical waveguides for example.

The soldering seam is preferably formed by an iron-based solder, i.e. a solder material based on iron. An iron-based solder contains, for example, approximately 28 to 35 percent by weight of iron and also further constituents, which are contained in smaller proportions by weight than iron. An iron-based solder of this kind, designated B—FeCrNiSiP-1027/1097 according to EN ISO 3677, is sold, for example, by Innobraze (Esslingen, Germany) under the name ML 7813/S. Iron-based solder is biocompatible, non-corroding and has favorable flow characteristics, and chromium plating is unnecessary. Moreover, by using iron-based solder, it is easily possible to ensure that the soldering seams are substantially free of gaps and fluid-tight. With iron-based solder, it is likewise possible to obtain a particularly smooth surface of the soldering seams, although a smoothing and/or overwelding of the soldering seams, for example by plasma welding, may additionally be performed. The fact that the soldering seam is made of iron-based solder means that it is possible, in a simple and reliable way, to achieve a permanent connection between the base blade and the tube, wherein the requirements placed on medical instruments and in particular on laryngoscope blades can be met at the same time.

Advantageously, the tube with the longitudinally extending corrugation and the outer face of the base blade are shaped in such a way that the volume of the cavity is suitable for receiving at least a quantity of solder material that is sufficient for forming the two soldering seams, in particular for forming soldering seams that are free of gaps. It is thus permitted that the entire quantity of solder material needed is arranged inside the cavity. This is particularly advantageous when using iron-based solder as solder material. In this way, it is easy to obtain a secure connection of the tube to the base blade and the formation of smooth soldering seams that are free of gaps. The reliability of the soldering process can be further improved in this way.

The base blade is preferably configured as a longitudinally extending, approximately partially cylindrical hollow profile, for example approximately semi-cylindrical or more or less in the shape of a hollow cylinder, which has a continuous longitudinal slit. The base blade thus forms a continuous, for example partially cylindrical interior which, during the use of the laryngoscope blade, can serve to permit an unimpeded view and to receive an intubation hose, for example. In a distal end region, the base blade can form an aperture through which a distal portion of the tube protrudes into the interior of the base blade, for example in order to permit illumination of the region of the patient's body viewed through the interior. Moreover, according to this embodiment, which in particular represents a Miller laryngoscope blade, a blade head is arranged in a proximal end region of the base blade, into which blade head there leads the proximal end of the tube arranged at least in part on the outer face of the base blade. The blade head is preferably attached to the outer face of the base blade. The blade head is configured for the attachment of a handle, which can be connected to the blade head by a latching connection, for example. Such a configuration of the laryngoscope blade makes it possible to create at the same time, within the blade head, a connection of the interior of the tube to an external power supply device, which can be attached to the handle. Thus, for example, the blade head can be configured to couple illumination light, which is generated by a light source arranged in or attached to the handle, into optical waveguides that are routed inside the tube.

According to a particularly preferred embodiment of the invention, the base blade has a longitudinally extending corrugation on the outside, wherein the tube and the base blade are arranged relative to each other in such a way that the respective corrugations face each other. The tube, in particular in at least parts thereof, is fitted onto or inserted into the corrugation of the base blade. In particular, the corrugation of the tube and the corrugation of the base blade together form the cavity. In this way, it is particularly easy for a cavity to be created which has a sufficient volume and which is of a shape suitable for the introduction of the solder material, wherein at the same time the soldering gaps are formed in which the soldering seams are provided for connecting the tube to the base blade. In this way too, neither the remaining interior of the tube nor the interior of the base blade is restricted excessively by the respective corrugations.

According to a preferred embodiment of the invention, a width of the corrugation of the tube is at least approximately equal to a width of the corrugation of the base blade. The respective width is measured transversely with respect to the longitudinal extent of the tube or of the base blade. According to this embodiment, the edge regions of the two corrugations are thus mounted on each other, and the soldering gaps are formed between the mutually corresponding edge regions of the two corrugations. The base blade and the tube have linear joining regions in particular. This permits simple and reliable execution of the soldering process, and particularly little solder material is needed.

According to a further preferred embodiment of the invention, the width of the corrugation of the tube is smaller than the width of the corrugation of the base blade, wherein the width is in each case measured transversely with respect to the longitudinal extent. In this way, it is possible to lay the tube into the corrugation of the base blade, which further simplifies assembly. Here too, the joining regions can be of a linear configuration, for example.

Particularly preferably, an inner radius of the corrugation of the base blade is approximately equal to an outer radius of the tube. The inner radius of the corrugation of the base blade is the radius of curvature, measured in cross section, of the outer surface of the base blade inside the corrugation, and the outer radius of the tube is the radius of curvature, measured in cross section, of the surface of the tube in the regions adjacent to the corrugation of the tube. In the case where the tube has a circular circumference with a concave portion formed by the corrugation, the inner radius of the corrugation of the base blade is approximately equal to the radius of the circular circumference of the tube. It is particularly advantageous here if the width of the corrugation of the tube is smaller than the width of the corrugation of the base blade. According to this embodiment, the tube thus lies in the corrugation of the base blade in such a way that wall regions of the tube that are adjacent to the corrugation still lie inside the corrugation of the base blade and, since the respective radii are approximately equal, form an approximately uniform soldering gap. In this case, the respective joining regions between which the soldering seams are formed are two-dimensional regions. In this way, a particularly reliable and fluid-tight connection can be created between the tube and the base blade.

In a method according to the invention for producing a laryngoscope blade, a first step involves making available a base blade, which on the outside can have a corrugation extending in the longitudinal direction of the base blade, and a tube, which at least in part has a corrugation extending in the longitudinal direction. The base blade and the tube are in particular configured as described above.

In a second step, the tube is held at the base blade in order to form a cavity between the corrugation of the tube and the outer surface of the base blade, such that a soldering gap is formed on both sides of the cavity. For this purpose, the tube is in particular held relative to the base blade in such a way that the respective joining regions of the tube and of the base blade are at a slight distance from each other. Moreover, solder material is arranged in the cavity. The solder material is preferably an iron-based solder in the form of a paste, for example the iron-based solder ML 7813/S from Innobraze (Esslingen, Germany). The solder material is in particular arranged in such a way that it lies at least in part on both sides of the cavity both on the outer face of the base blade and on the corrugation of the tube; the solder material can also partially fill the cavity. In this way, the solder material is in capillary connection to the two soldering gaps formed to both sides of the corrugation of the tube.

In a third step, the resulting structure composed of the base blade and tube and of the solder material, which structure is also designated as a "solder bond", is introduced into a furnace and is there heated to a soldering temperature, i.e. in particular to a temperature that corresponds at least to the melting temperature of the solder material but lies below a melting temperature of the material of the base blade and of the tube. The solder bond can be heated to the soldering temperature, for example under vacuum or a protective gas. The solder material thus liquefies, any auxiliary substances evaporate and the liquid solder is drawn by capillary forces into the soldering gaps formed between the tube and the base blade and fills these gaps.

After the solder has filled the two soldering gaps, the solder bond is allowed to cool until the solder material has hardened and the tube and the base blade are firmly connected to each other by the soldered connection.

The method can comprise further steps, in particular steps for producing the base blade and the tube and final production steps after the laryngoscope blade has cooled. For example, the tube can be produced from a cylindrical tube into which a longitudinally extending corrugation is impressed in parts. The base blade can be produced from a corresponding blank, in the outer face of which a longitudinally extending corrugation can likewise be impressed in parts. Moreover, the distal end of the base blade can be given an atraumatic shape in a manner known per se. Furthermore, a preliminary treatment of the components to be connected to each other or of the joining regions can be provided. After the solder bond has cooled, optical waveguides for example can be inserted into the tube, preferably from the distal direction, and the tube can be sealed off by filling with adhesive.

By means of the method according to the invention, it is possible, in a simple and reliable way, to produce a laryngoscope blade, for example a Miller laryngoscope blade, which meets the requirements placed on laryngoscope blades in terms of their use, cleaning and sterilizing.

According to a preferred embodiment of the method, in the second step the distal portion of the tube is first of all inserted into an aperture formed in the distal end region of the base blade, after which a middle portion is placed onto the base blade and is then held on the base blade, for example with two laser weld spots arranged in the proximal end region, in such a way that the corrugation of the tube forms the cavity together with the surface of the base blade and the soldering gaps are formed in the edge regions of the corrugation. It is particularly advantageous here if the distal end portion of the tube is angled downward in relation to the middle portion, for which purpose the tube can be suitably bent in a preparatory step. The tube does not need to have a corrugation in the angled distal end portion. If the base blade itself has a longitudinally extending corrugation, the aperture is arranged in the distal continuation of this corrugation, and the tube is placed onto or into the corrugation of the base blade and held in this position. The production method can be further simplified thereby.

In a first subsidiary step of the second step, the tube is preferably held to form the cavity, and then, in a second subsidiary step, the solder material is introduced into the cavity, in particular from the proximal direction. This embodiment of the method is particularly simple and reliable. Alternatively, the solder material can initially be arranged in the corrugation of the tube and/or on the surface of the base blade, after which the tube can then be placed onto the base blade.

Particularly preferably, provision can be made that the solder material is applied with a dosing device, for example with an applicator which comprises a dosing device and a syringe needle. In particular, the solder material is introduced into the cavity from the proximal direction and fills a proximal region of the cavity. The fact that the entirety of the required solder material is introduced into the cavity is advantageous when iron-based solder is used. The dosing device is configured to discharge the required quantity of solder material, and the syringe needle is adapted to introduce the solder material into the cavity from the proximal direction. In this way, it is easily possible to apply the desired quantity of solder material needed to generate the soldering seams, which permits particularly reliable execution of the method for creating clean and smooth soldering seams.

According to a preferred embodiment of the method, in the second step, after the tube has been held at the base blade and the solder material has been introduced, a blade head is attached to a proximal end region of the base blade, in particular to the outer face of the base blade, wherein the tube can be inserted into a corresponding bore of the blade head. The blade head can be fixed to the base blade, for example likewise with laser weld spots, and solder material can be applied to the resulting soldering gaps of the blade head. In the third step, a soldered connection can also be produced in this way between the blade head and the base blade and the tube.

It will be appreciated that the aforementioned features and the features still to be explained below can be used not only in the respectively cited combination but also in other combinations or singly, without departing from the scope of the present invention.

BRIEF DESCRIPTION OF THE DRAWINGS

Further aspects of the invention will become clear from the following description of a preferred illustrative embodiment and from the attached drawing, in which:

FIGS. 2a to 2c show three different views of a variant of the illustrative embodiment according to FIGS. 1a and 1b;

FIG. 3 shows a cross section through the light channel tube of the laryngoscope blade according to FIGS. 1a and 1b and of the variant according to FIGS. 2a to 2c;

FIG. 4 shows a cross-sectional view of the laryngoscope blade according to FIGS. 1a and 1b and according to FIGS. 2a to 2c;

DETAILED DESCRIPTION

Figure 1A:
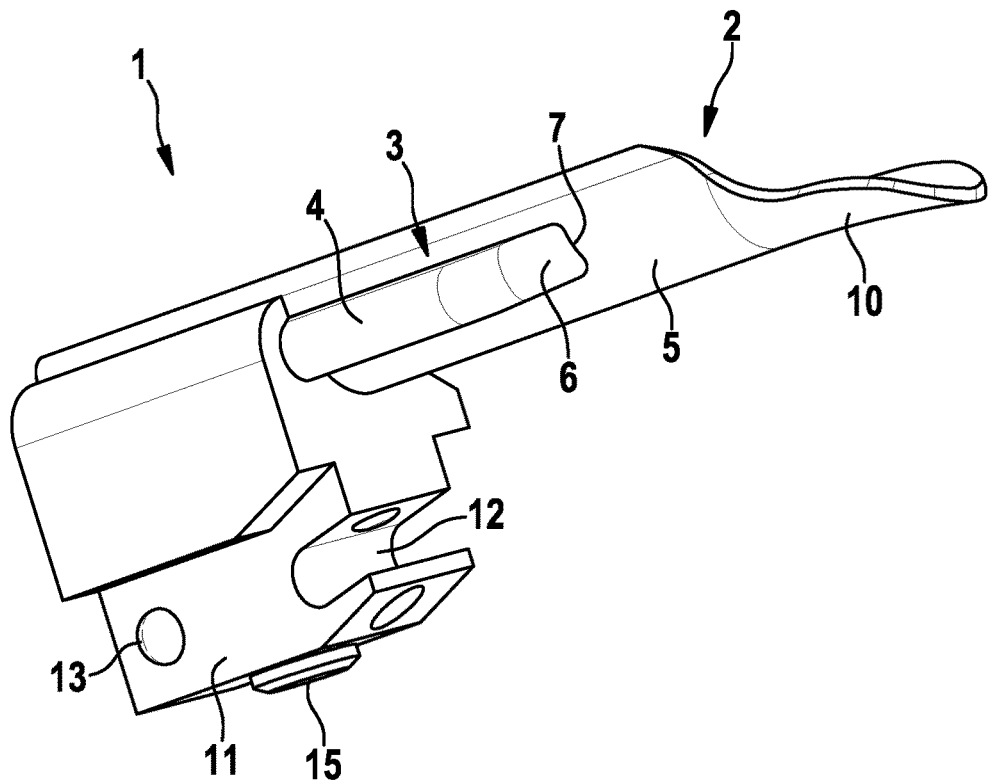
FIGS. 1a and 1b show two different views of an illustrative embodiment of a laryngoscope blade according to the invention.
Figure 1B:
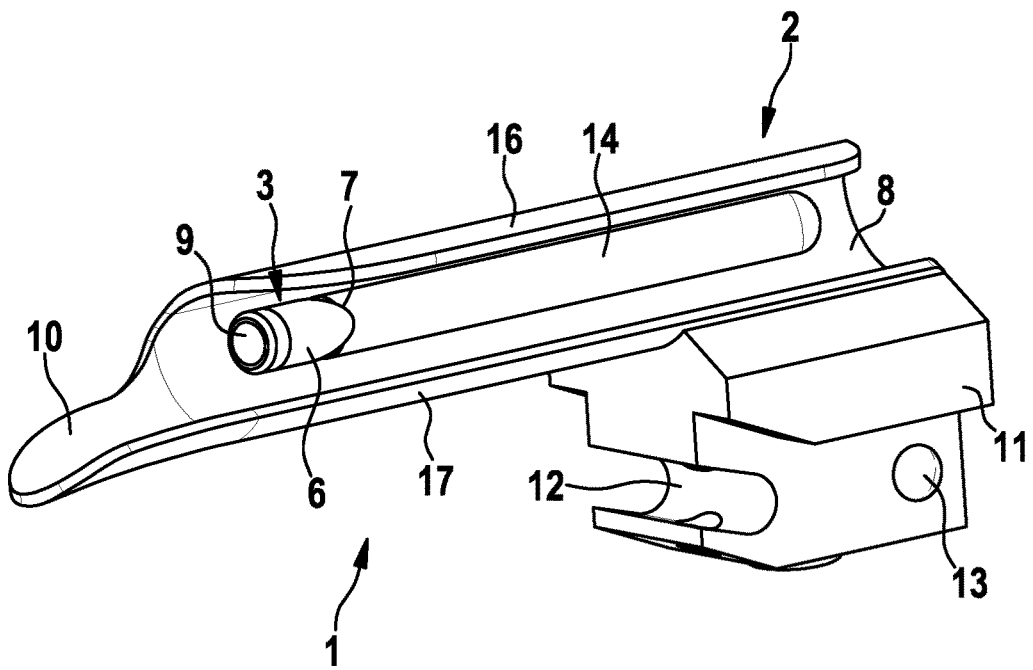

In FIGS. 1a and 1b, an illustrative embodiment of a laryngoscope blade according to the invention is shown in two oblique views. The laryngoscope blade 1 is configured as a Miller laryngoscope blade and has a base blade 2 of approximately semicylindrical shape. Connected firmly to the base blade 2 is a light channel tube 3 which, in a middle portion 4, is arranged on an outer face 5 of the base blade 2 and extends parallel to the longitudinal direction of the base blade 2. A distal portion 6 of the light channel tube 3 is angled in relation to the middle portion 4 and passes through an aperture 7 to the inside 8 of the base blade 2. Optical fibers for carrying illumination light extend inside the light channel tube 3 and open out in a light exit surface 9 at the distal end of the light channel tube 3. The distal end of the base blade 2 is configured as a spoon-shaped continuation 10. The edges of the continuation 10, and also the other edges of the base blade 2, are rounded to prevent trauma.

Arranged at the proximal end of the base blade 2 is a blade head 11, which is firmly connected to the base blade 2. A handle (not shown) can be attached to the blade head 11 by way of a transverse groove 12 and spring-mounted catches 13, which handle then protrudes downward approximately perpendicularly from the base blade 2. In accordance with the views shown in FIGS. 1a and 1b, the word "downward", here and in the text below, designates the direction in which the blade head 11 and the handle, when attached, protrude from the base blade 2, and "upward" designates the opposite direction: "downward" and "upward" refer here only to the position of the structural parts relative to each other, not to the orientation of the laryngoscope blade 1 during the use thereof. Accordingly, in the illustrative embodiment shown, when viewed from the proximal direction, the base blade 2 is open on the left, while the light channel tube 3 is arranged on the right.

The base blade 2 has a longitudinally extending corrugation which is impressed into the outer face 5 and into which the light channel tube 3 is placed, and which corrugation can be seen on the inner face 8 as a longitudinally extending bead 14 (see FIG. 1b). The corrugation or the bead 14 divides the base blade 2 into an upper wing 16 and a lower wing 17. A proximal portion of the light channel tube 3 is fitted into the blade head 11. The optical fibers guided in the light channel tube 3 extend in a curved configuration inside the blade head 11 and lead into a light connector face 15. A corresponding light coupling face of the handle can be attached to the light connector face 15 in order to couple illumination light into the optical fibers of the light channel tube 3, which optical fibers carry the illumination light to the light exit face 9.

The base blade 2 and the light channel tube 3 are each made of stainless steel and are connected to each other by soldering with iron-based solder. The blade head 11 is also made of stainless steel and connected to the base blade 2 and to the light channel tube 3 by soldering with iron-based solder.

FIGS. 2a to 2c show three different views of a variant of the illustrative embodiment described above. This variant differs from the variant shown in FIGS. 1a and 1b only in terms of the length of the base blade 2 and the corresponding length of the middle portion 4 of the light channel tube 3. In other respects, the two variants are of identical configuration. The variant of FIGS. 1a and 1b can be, for example, a laryngoscope blade for children (size 0 or 1), while the variant shown in FIGS. 2a to 2c is a laryngoscope blade for adults (size 3 or 4).

FIG. 2a shows a side view of the laryngoscope blade 1 seen from the left, FIG. 2b shows a side view seen from above, and FIG. 2c shows a view from the proximal direction. FIG. 2a shows that the spoon-shaped continuation 10 is angled slightly downward. As can be seen from FIG. 2b, the distal portion 6 of the light channel tube 3 with the light exit face 9 is angled slightly to the left. In this way, a region can be illuminated that is arranged distally of the laryngoscope blade 1 and offset slightly to the left. FIG. 2c shows that the upper wing 16 is slightly narrower than the lower wing 17; both of them together form what is approximately a half cylinder and, measured from a longitudinal axis of the half cylinder, occupy an arc of slightly more than 180°. In the upper region, the upper wing 16 has a slightly more pronounced inward curvature.

FIG. 3 shows a cross section through the light channel tube 3, in the middle portion 4 thereof. The light channel tube 3 has a substantially cylindrical configuration, with a circular outer contour along most of the circumference, wherein a corrugation 18 is impressed at one side. The interior 24, which is limited only slightly by the corrugation 18, serves to receive the optical fibers. The angled distal portion 6 of the light channel tube 3 has no corrugation (see FIGS. 1a to 2b).

In the assembled state, the light channel tube 3 is inserted into the aforementioned corrugation of the base blade 2, specifically in such a way that the corrugation 18 of the light channel tube 3 is directed toward the base blade 2 or the corrugation of the base blade 2. This is depicted in the cross-sectional view in FIG. 4 which, seen obliquely from the distal direction, shows a section through the base blade 2 and the light channel tube 3. As is shown in FIG. 4, the corrugation 18 of the light channel tube 3 has a smaller width than the corrugation 19 of the base blade. The radius of curvature of the surface of the base blade 2 in the interior of the corrugation 19 corresponds approximately to the radius of the circular outer contour of the light channel tube 3, such that the light channel tube 3 inserted into the corrugation 19 of the base blade 2 bears two-dimensionally on the base blade 2 to both sides of the corrugation 18 or forms soldering gaps 20, 20' of approximately uniform width to both sides of the corrugation 18. The regions of the surface of the light channel tube 3 located to both sides of the corrugation 18 and the regions opposite them inside the corrugation 19 of the base blade 2 serve as joining regions. The corrugation 18 of the light channel tube 3 forms, with the other part of the corrugation 19 of the base blade 2, a cavity 21.

The cavity 21 serves to receive the solder material prior to the soldering process. The two soldering gaps 20, 20' are of such a width that, during the soldering process, the iron-based solder used as solder material penetrates into the soldering gaps 20, 20', spreads over the entire length of the soldering gaps 20, 20' and fills them, said width being, for example, ca. 0.03 to 0.05 mm. This not only results in a firm connection of the light channel tube 3 to the base blade 2, it provides on the outer face of the soldering gaps 20, 20' a soldering seam with a smooth surface free of gaps. In particular, sufficient solder material is introduced into the cavity 21 such that the distal portion 6 of the light channel tube 3 is also surrounded by a soldering seam in the aperture 7 (see FIGS. 1a and 1b). In this way, the cavity 21 is at the same time closed off at the distal end. Moreover, the blade head 11 is connected by soldering to the base blade 2 and to the light channel tube 3, as a result of which the cavity 21 can also be closed at the proximal end.

Figure 5:
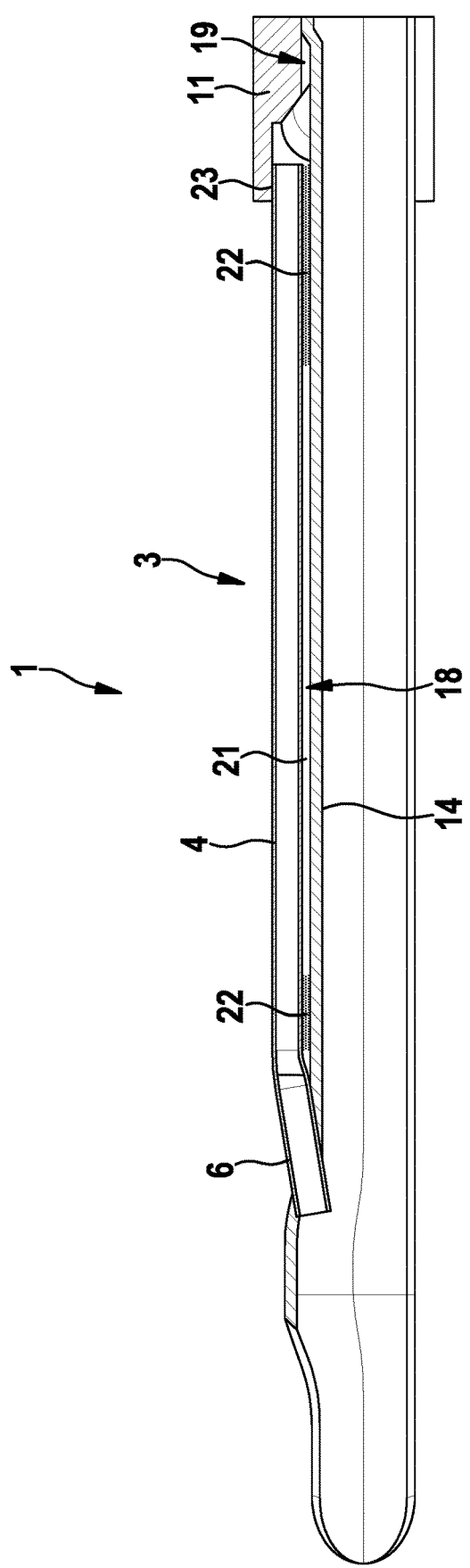
FIG. 5 shows a longitudinal section of the laryngoscope blade according to FIGS. 2a to 2c.

The longitudinal section of the laryngoscope blade 1 in FIG. 5 shows that the cavity extends from the proximal end of the light channel tube 3 as far as the transition between the middle portion 4 and the angled distal portion 6 of the light channel tube 3. The solder material 22 introduced prior to the soldering process is indicated symbolically. According to FIG. 5, the solder material can be arranged in a distal region and in a proximal region of the cavity 21, although it generally suffices to introduce the solder material into the proximal region of the cavity 21. It will also be seen from FIG. 5 that the light channel tube 3 protrudes with its proximal portion 23 into the blade head 11, and that the corrugation 19 of the base blade 2 or the bead 14 extends in the proximal direction slightly beyond the proximal end of the light channel tube 3.

According to an illustrative embodiment of the method according to the invention, the laryngoscope blade 1 is produced by first of all making available the base blade 2, the light channel tube 3 and the blade head 11. The light channel tube 3 is pushed with its angled distal portion into the aperture 7 of the base blade 2 and then fitted into the corrugation 19 of the base blade 2 and in this position, in which soldering gaps 20, 20' are present to both sides of the corrugation 18 of the light channel tube, is bonded at or near its proximal portion 23 to the base blade 2 by way of two laser weld spots. With an applicator which comprises a dosing device and a syringe needle, iron-based solder in the form of a solder paste is then introduced from the proximal direction into the cavity formed between the corrugation 18 of the light channel tube 3 and the base blade 2, until said cavity is filled with the solder material in a proximal region; optionally, a distal region can also be filled with solder material (see FIG. 5). Moreover, the blade head 11 is attached to the proximal end region of the base blade 2, such that the proximal portion 23 extends into the blade head 11, and is likewise secured to the base blade 2 with laser weld spots; solder material can likewise be arranged at the corresponding soldering gaps of the blade head 11.

This solder bond is introduced into a furnace and heated to a soldering temperature of approximately 1120° C. The iron-based solder thus liquefies and flows, on account of the capillary action, into the soldering gaps 20, 20' and into corresponding soldering gaps of the blade head 11. Similarly, the gap between the aperture 7 and the distal portion 6 of the light channel tube is filled with solder. During the subsequent cooling, which can take place over the course of an hour or a few hours for example, the iron-based solder hardens in the soldering gaps and forms soldering seams, whereby a firm, durable and gap-free connection is created between the components to be connected to one another. The resulting soldering seams have a smooth surface, such that only minor after treatment is generally needed, if indeed any.

Once cooling is complete, optical waveguides are pushed from the distal direction into the light channel tube 3 and farther into the blade head 11. Finally, the light exit face 9 and the light connector face 15 are created by filling with adhesive and by subsequent working.

For the sake of clarity, not all the reference signs are shown in all of the figures. Reference signs not explained in connection with one figure have the same meaning as in the other figures.

The invention claimed is:
1. A laryngoscope blade comprising
a base blade, and
a tube which is arranged at least in part on an outer face of the base blade, and extends approximately in a longitudinal direction of the base blade and is firmly connected to the base blade,
characterized in that the tube, at its side facing toward the base blade, has at least in part a longitudinally extending corrugation which, with the outer face of the base blade, forms a longitudinally extending cavity,
wherein the tube is connected to the base blade by a respective soldering seam in lateral edge regions of the corrugation, and
the corrugation includes two edge regions, and the cavity is formed between the two edge regions.
2. The laryngoscope blade as claimed in claim 1, wherein the soldering seam is formed by iron-based solder.
3. The laryngoscope blade as claimed in claim 1, wherein the volume of the cavity is dimensioned at least to receive a quantity of solder material that is sufficient for forming the soldering seams.
4. The laryngoscope blade as claimed in claim 1, wherein the base blade is configured as a longitudinally extending, approximately partially cylindrical hollow profile, wherein a blade head, into which the tube leads, is arranged at a proximal end region of the base blade.
5. The laryngoscope blade as claimed in claim 1, wherein the base blade has a longitudinally extending corrugation on the outside, and in that the corrugation of the tube and the corrugation of the base blade are directed toward each other.
6. The laryngoscope blade as claimed in claim 5, wherein a width of the corrugation of the tube is smaller than or approximately equal to a width of the corrugation of the base blade.
7. The laryngoscope blade as claimed in claim 5, wherein an inner radius of the corrugation of the base blade is at least approximately equal to an outer radius of the tube.

8. The laryngoscope blade as claimed in claim 2, wherein the volume of the cavity is dimensioned at least to receive a quantity of solder material that is sufficient for forming the soldering seams.

9. The laryngoscope blade as claimed in claim 2, wherein the base blade has a longitudinally extending corrugation on the outside, and in that the corrugation of the tube and the corrugation of the base blade are directed toward each other.

10. The laryngoscope blade as claimed in claim 6, wherein an inner radius of the corrugation of the base blade is at least approximately equal to an outer radius of the tube.

11. The laryngoscope blade as claimed in claim 1, wherein the cavity is formed at least partially by a concavity in the tube.

12. The laryngoscope blade as claimed in claim 1, wherein the cavity holds solder during manufacturing and the solder fills soldering gaps on the sides of the cavity to solder the tube to the base blade.

13. The laryngoscope blade as claimed in claim 1, wherein the tube is closed all the way around its circumference.

14. The laryngoscope blade as claimed in claim 1, wherein the tube comprises a round cross-section.

15. The laryngoscope blade as claimed in claim 1, wherein the tube is produced from a cylindrical tube.

16. A laryngoscope blade comprising
a base blade,
a tube which is arranged at least in part on an outer face of the base blade, and extends approximately in a longitudinal direction of the base blade and is firmly connected to the base blade,
characterized in that the tube, at its side facing toward the base blade, has at least in part a longitudinally extending corrugation which, with the outer face of the base blade, forms a longitudinally extending cavity,
the tube is connected to the base blade by a respective soldering seam in lateral edge regions of the corrugation,
the corrugation includes a furrow-like depression in the tube.

17. A laryngoscope blade comprising
a base blade,
a tube which is arranged at least in part on an outer face of the base blade, and extends approximately in a longitudinal direction of the base blade and is firmly connected to the base blade,
characterized in that the tube, at its side facing toward the base blade, has at least in part a longitudinally extending corrugation which, with the outer face of the base blade, forms a longitudinally extending cavity,
the tube is connected to the base blade by a respective soldering seam in lateral edge regions of the corrugation,
the tube includes a circumferential cross-section that is concave in the region of the corrugation and otherwise is convex.

* * * * *